(12) United States Patent
Ahn et al.

(10) Patent No.: US 12,298,224 B2
(45) Date of Patent: May 13, 2025

(54) ADVANCED CORROSION BIOREACTOR TESTING APPARATUS

(71) Applicant: Syracuse University, Syracuse, NY (US)

(72) Inventors: Jeongmin Ahn, Manlius, NY (US); Thomas Welles, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 256 days.

(21) Appl. No.: 18/120,246

(22) Filed: Mar. 10, 2023

(65) Prior Publication Data

US 2023/0314303 A1 Oct. 5, 2023

Related U.S. Application Data

(60) Provisional application No. 63/318,416, filed on Mar. 10, 2022.

(51) Int. Cl.
*G01N 17/00* (2006.01)
*A61F 2/46* (2006.01)
*G01N 3/60* (2006.01)

(52) U.S. Cl.
CPC .......... *G01N 17/002* (2013.01); *A61F 2/468* (2013.01); *G01N 3/60* (2013.01); *G01N 17/006* (2013.01)

(58) Field of Classification Search
CPC ...... G01N 17/002; G01N 17/006; G01N 3/08; G01N 3/60; A61F 2/468
See application file for complete search history.

(56) References Cited

U.S. PATENT DOCUMENTS 6,865,954 B2 * 3/2005 Zubok ............... G01N 3/56
73/804
7,219,555 B2 * 5/2007 Salvesen ............ A61F 2/468
73/788

(Continued)

FOREIGN PATENT DOCUMENTS

CN 206930536 U * 1/2018
CN 109187181 A * 1/2019

(Continued)

OTHER PUBLICATIONS

Machine translation of CN113974925 (Year: 2022).*
Machine translation of DE29911169 (Year: 1999).*

*Primary Examiner* — Natalie Huls
(74) *Attorney, Agent, or Firm* — David L. Nocilly; Bond, Schoeneck & King PLLC

(57) ABSTRACT

A testing apparatus for evaluating a medical implant for electric potential oscillations that lead to corrosion. The testing apparatus uses a uniaxial load device having a mounting base for accepting a medical implant and orienting the implant along a predetermined axis, a support plate positioned under the uniaxial load device and moveable to apply a force to the implant, a load cell positioned above the mounting plate to measure the force applied to the implant, and a set of differential variable reluctance transducers positioned to measure motion of the implant. A chamber encloses the uniaxial load device so that the implant can be submerged in a fluid replicating human synovial fluid. A faraday cage surrounds the chamber for isolation from environmental electromagnetic radiation. An array of near field antenna are positioned circumferentially around the chamber and driven by a multi-frequency generator.

12 Claims, 1 Drawing Sheet

(56) References Cited

U.S. PATENT DOCUMENTS

| | | | | |
|---|---|---|---|---|
| 8,528,415 B2 * | 9/2013 | McKnight | ............... | G01N 3/22 |
| | | | | 73/818 |
| 12,186,208 B2 * | 1/2025 | Ahn | ..................... | G01R 23/00 |
| 2008/0257057 A1 * | 10/2008 | Habeger | .................. | G01N 3/32 |
| | | | | 73/808 |
| 2015/0057809 A1 * | 2/2015 | Deck | ..................... | G06N 20/00 |
| | | | | 700/275 |

FOREIGN PATENT DOCUMENTS

| | | | | |
|---|---|---|---|---|
| CN | 111398020 A | * | 7/2020 | ........... C12N 5/0654 |
| CN | 113974925 A | * | 1/2022 | ............. A61F 2/389 |
| CN | 108132185 B | * | 10/2023 | ............... G01N 3/02 |
| DE | 29911169 U1 | * | 10/1999 | ............. A61F 2/468 |
| KR | 101095195 B1 | * | 12/2011 | ............. A61F 2/468 |
| KR | 20170029368 A | * | 3/2017 | ........... A61C 8/0098 |

* cited by examiner

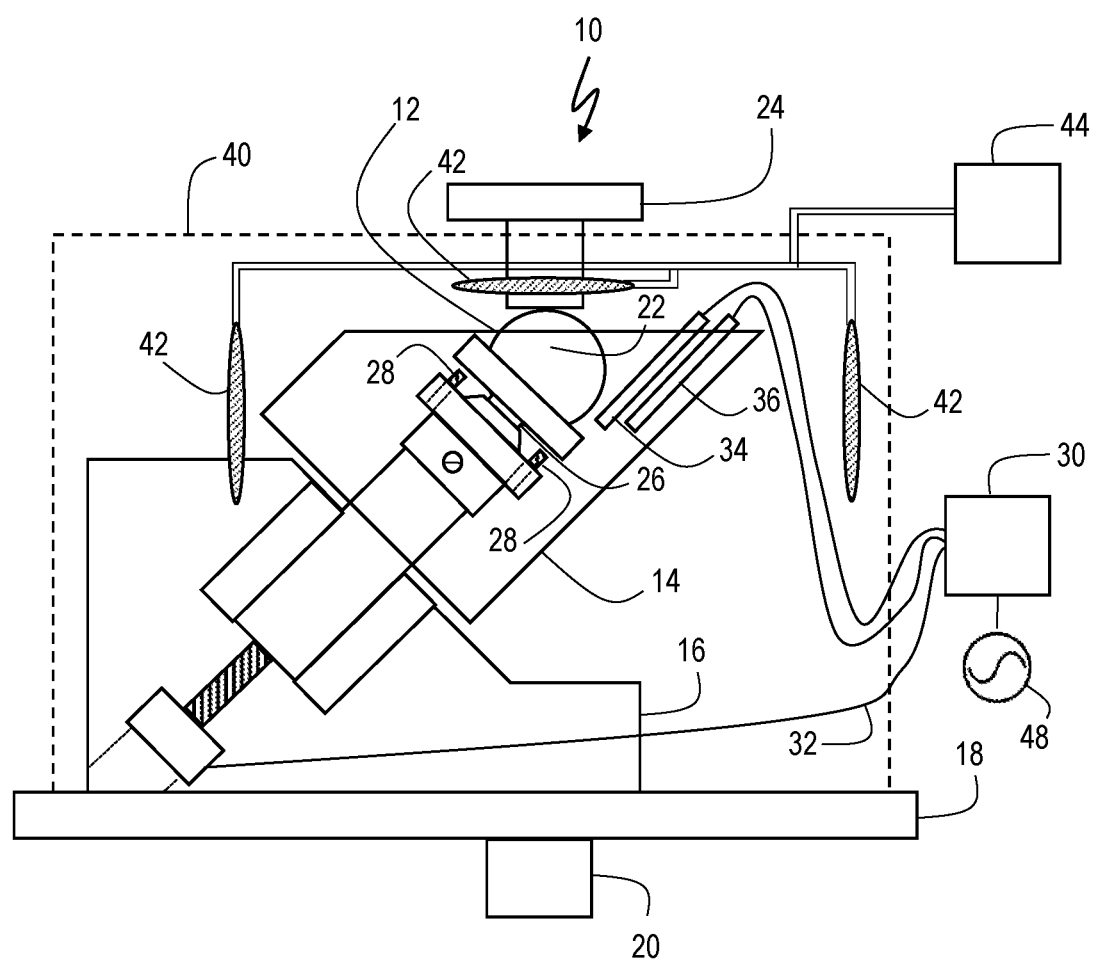

ADVANCED CORROSION BIOREACTOR TESTING APPARATUS

CROSS-REFERENCE TO RELATED APPLICATIONS

The present application claims priority to U.S. Provisional Application No. 63/318,416, filed on Mar. 10, 2022.

BACKGROUND OF THE INVENTION

1. Field of the Invention

The present invention relates to modular hip implants and, more specifically, to a testing apparatus that can simulate in vivo conditions under which corrosion may occur.

2. Description of the Related Art

Total hip arthroplasty (THA) has been considered to be the most successful operation to both relieve pain and restore mobility from osteoarthritis; however, implant corrosion and wear-related complications remain a daily concern for implant longevity and patient health. 2 In the U.S. alone, there are over 370,000 THAs performed annually, and it is predicted that over 3 million individuals are currently living with a hip implant.

Current state of the art THA implants are comprised of cobalt-chromium-molybdenum and/or titanium-aluminum-vanadium alloys and are designed to prevent hip dislocation and polyethylene wear complications. A particular type of THA, known as the metal-on-metal (MoM hip) implant, however, was found to be associated with severe inflammatory reactions of the periprosthetic soft tissues described as adverse local tissue reactions (ALTR). ALTRs have since been associated with modular taper junctions, a near universally used design element in THAs. Such increased tribocorrosion reactions can lead to increased generation of corrosion and wear debris, and may result in extensive tissue necrosis, injury to abductor muscles and tendons, aseptic loosening/osteolysis, increased revision complications, and significant patient morbidity. For the MoM generation of implant, it was reported that for every 100 hip replacement surgeries, there were approximately 18 hip revision surgeries, costing on average, $39,000 and 2-3 hours of surgical time per event. One growing cause of THA revision is tissue inflammation associated with implant tribocorrosion. Therefore, inadequate understanding of implant corrosion and wear could result in a total economic impact of $7 billion USD and 360,000 surgical hours.

Release of metal ions from implant interfaces into the local tissues and bloodstream may result in toxicity, inflammation, and local tissue necrosis. Unfortunately, current research, which most commonly cites fretting and crevice corrosion to be the cause of implant failure, does not perfectly describe or predict the corrosive breakdown seen in recovered orthopedic implants. Fretting theories indicate that corrosion occurs when the natural passivation/oxide film is broken down via mechanical damage. Crevice corrosion can subsequently accelerate the corrosion of the material at the interface between femoral head and modular femoral neck. Although fretting and crevice corrosion are present at the modular junction, studies often focus only on tribological factors and fail to assess the crevice corrosion elements of the process.

While extensive work has been conducted in the study of tribocorrosion or mechanically assisted crevice corrosion, the type and extent of corrosion observed in failed modular tapers have not yet been reproduced in vitro, nor have the basic physical-chemical-biological processes resulting in the observed corrosion behavior in vivo. Recent studies have indicated that electric potential oscillations may contribute to the complex corrosion seen on THA implants. Accordingly, there is a need for a device and system that can recreate the conditions under which corrosion can occur to evaluate new devices and implants for potential failure.

BRIEF SUMMARY OF THE INVENTION

The present invention is a testing apparatus that can simulate the in vivo condition of a modular hip implant to recreate the conditions in the human body. The present invention may thus be used to evaluate whether how various factors, such as electrical potential oscillations, contribute to corrosion in the taper junction. The testing apparatus includes a uniaxial load device having a mounting base for accepting a medical implant and orienting the implant along a predetermined axis, a support plate positioned under the uniaxial load device and moveable to apply a force to the implant, a load cell positioned above the mounting plate to measure the force applied to the implant, and a set of differential variable reluctance transducers positioned to measure motion of the implant. A chamber encloses the uniaxial load device so that a fluid simulating human synovial fluid can submerge an implant positioned in the uniaxial load device. A faraday cage is used to electrically isolate the chamber from environmental electromagnetic radiation. An array of near field antenna are coupled to a multi-frequency generator and positioned circumferentially around the chamber to create the electric potential oscillations in the implant while it is submerged and placed under load, thereby replicating conditions likely to be experienced in vivo.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of an in vitro testing apparatus for THA implants according to the present invention.

DETAILED DESCRIPTION OF THE INVENTION

Referring to the FIGURES, wherein like numerals refer to like parts throughout, there is seen in FIG. 1 an in vitro test cell 10 including a uniaxial load apparatus along with electronic equipment required to induce and control electric potential oscillations of an implant that is being tested using the uniaxial load apparatus. Utilization of actual modular junctions increases the likelihood of accurately capturing the expected 3D effects of induced electric potential oscillations while simultaneously allowing for direct comparison to recovered implants.

As seen in FIG. 1, a corrosion test specimen 12 is fixed at the bottom of a test chamber 14 into a mounting base 16. Mounting base 16 orients the test specimen for loading along an axis that is 35° from vertical to accurately replicate human physiology. Mounting base 16 is placed upon a support plate 18 which may be moved by a hydraulic actuator 20, providing a uniaxial upward force. The femoral head 22 of test specimen 12 is held against a load cell 24 to record applied force. Micro-motion at the modular junction 26 is recorded by a set of differential variable reluctance transducers (DVRTs) 29 to quantify the degree of fretting driven corrosion.

Modular junction 26 is contained within controlled environmental test chamber 14, as seen in FIG. 1, mimicking the synovial fluid environment. Test chamber 14 is placed around test specimen 12 so that modular junction 26 remains submerged throughout testing. Electrochemical behavior is monitored by an EIS capable potentiostat 30 in a traditional 3-probe setup. Corrosion test specimen 12 acts as the working electrode 32. Standard reference 34 and counter electrodes 36 are then be inserted into the simulated synovial fluid of test chamber 14 proximally to test specimen 12.

Testing apparatus 10 is further modified to incorporate the ability of inducing electric potential oscillations on the implant, thereby driving the proposed corrosion mechanism concurrently with fretting corrosion. For example, a faraday cage 40 is constructed around testing apparatus 10 to prevent ambient electromagnetic radiation from interacting with the test specimen. An array of near field antennas 42 is placed circumferentially around the environmental chamber. Near field antennas 42 are connected to a multi-channel signal frequency generator 44 to emit a specified electric field. A minimum of five near field antennas 42 are preferable used so that electric fields may be sourced above and on each side of test chamber 12. Each antenna within array 42 may be activated individually or simultaneously. Multi-channel frequency generator 44 is preferable capable of individually activating each antenna within array 42 for precise control of both temporally and spatially varying electric fields. An oscilloscope 48 (or spectrum analyzer or other AC electric potential sensing device) may additionally be incorporated into testing apparatus 12 to record electric potential fluctuations induced across modular junction 16. Connection to an oscilloscope will be carefully controlled and synchronized with potentiostat operation 30 to prevent corruption of EIS data. Antenna of array 42 may comprise any type of electric field generating devices, including even moving magnets, to generate the requisite electric fields.

Testing apparatus 10 of the present invention allows for the independent and simultaneous investigation of both the proposed electrically driven corrosion and the current methods of fretting and crevice corrosion. Therefore, each corrosion mechanism can be individually investigated or selectively combined to investigate the contribution of each mechanism to the complete corrosion of the implant. The testing apparatus thus builds upon the current standard for fretting corrosion, and could be adopted across the medical implant industry for the evaluation of implants.

The present invention may be used to identify the potential for nonionizing, low magnitude electrical oscillations to preferentially excite harmonics of phonon vibrations and associated wave functions within the solid to manipulate the selected surface reaction that occurs. It is believed that the presence of EMFs incident on an electrically conductive material can manipulate the landscape of potential energy wells at the interface between the fluid film and conductive surface. The absorbed energy, insufficient to ionize the material, may couple with natural lattice vibrations/phonons, localized electron charging, defect locations, grain boundaries, or the natural periodicity of the crystal lattice to locally increase the relative potential energy. A concentration of localized energy creates a nucleation site for increased electrochemical activity; capable of bridging the passivation layer and broadening the probability of expected surface reactions.

Data developed from the present invention will allow for the classification of the recorded electrochemical reactions with respect to the frequency, magnitude, and exposure length of the electromagnetic field within the reaction zone. A 2-way analysis of variance (ANOVA) analysis and Tukey's honestly significant difference (HSD) test may then be performed on the collected experimental data to identify the significance of electromagnetic radiation source, magnitude of oscillation, and frequency of oscillation to the generation and classification of corrosion products. The corrosion products can be classified by: size, shape, topography, corrosion pattern, crystallinity, elemental composition, and fluid metal ion concentration. Post hoc analysis will identify the statistically relevant parameters of the effects of electromagnetic radiation in the generation of corrosion products on implanted biomedical metal alloys.

What is claimed is:

1. A testing apparatus, comprising:
a uniaxial load device having a mounting base for accepting a medical implant and orienting the medical implant along a predetermined axis, a support plate positioned under the uniaxial load device and moveable to apply a force to the medical implant, a load cell positioned above and oppositely to the support plate to measure any force applied to the medical implant, and a set of differential variable reluctance transducers positioned to measure motion of the implant;
a chamber enclosing the uniaxial load device and including a fluid therein that will completely submerge an implant positioned in the uniaxial load device;
an array of near field antenna positioned circumferentially around the chamber;
a faraday cage surrounding the chamber and isolating the uniaxial load device from environmental electromagnetic radiation; and
a multi-frequency generator coupled to the array of near field antenna.

2. The testing apparatus of claim 1, further comprising a potentiostat having a working electrode, a reference electrode, and a counter electrode.

3. The testing apparatus of claim 2, further comprising an oscilloscope coupled to the potentiostat.

4. The testing apparatus of claim 3, wherein the multi-frequency generator is configured to operate the array of near field antenna individual and simultaneously.

5. The testing apparatus of claim 4, wherein the fluid in the chamber comprises artificial human synovial fluid.

6. The testing apparatus of claim 5, wherein the predetermined axis is oriented at thirty-five degrees from vertical.

7. A method of testing a medical implant, comprising the steps of:
positioning the medical implant in a test assembly having a mounting base of a uniaxial load device that orients the medical implant and orienting the medical implant along a predetermined axis;
applying a force to the medical implant using a support plate positioned under the uniaxial load device;
measuring the force applied to the medical implant with a load cell positioned above and oppositely from the support plate;
measuring motion of the medical implant with a set of differential variable reluctance transducers;
enclosing the medical implant in a chamber that submerges a modular junction of the medical in a fluid;
energizing an array of near field antenna positioned circumferentially around the chamber with a multi-frequency generator; and isolating the test assembly from environmental electromagnetic radiation with a faraday cage surrounding the chamber.

8. The method of claim 7, further comprising the step of measuring an electrochemical response of the medical implant with a potentiostat having a working electrode, a reference electrode, and a counter electrode.

9. The method of claim 8, further comprising the step of analyzing the electrochemical response of the medical implant with an oscilloscope coupled to the potentiostat.

10. The method of claim 9, wherein multi-frequency generator is configured to operate the array of near field antenna individual and simultaneously.

11. The method of claim 10, wherein the fluid in the chamber comprises artificial human synovial fluid.

12. The method of claim 11, wherein the predetermined axis is oriented at thirty-five degrees from vertical.

* * * * *